(12) United States Patent
Huang et al.

(10) Patent No.: US 9,873,899 B2
(45) Date of Patent: Jan. 23, 2018

(54) **ISOLATED *PEDIOCOCCUS ACIDILACTICI* 05B0111 AND METHOD OF PRODUCING EXOPOLYSACCHARIDE**

(71) Applicant: Food Industry Research and Development Institute, Hsinchu (TW)

(72) Inventors: Tsung-Chen Huang, Hsinchu (TW); Hing-Yuen Chan, Toufen Town (TW); Shy-Yunn Wann, Hsinchu (TW); Fu-Mei Lin, Zhonghe (TW); Fwu-Ling Lee, Hsinchu (TW); Chii-Cherng Liao, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 152 days.

(21) Appl. No.: 14/799,100

(22) Filed: Jul. 14, 2015

(65) Prior Publication Data
US 2015/0329886 A1    Nov. 19, 2015

Related U.S. Application Data

(62) Division of application No. 12/818,316, filed on Jun. 18, 2010, now abandoned.

(30) Foreign Application Priority Data

Oct. 15, 2009    (TW) .............................. 98134914 A

(51) Int. Cl.
*C12P 19/04* (2006.01)
*C12R 1/01* (2006.01)
*A23L 33/135* (2016.01)

(52) U.S. Cl.
CPC ............. *C12P 19/04* (2013.01); *A23L 33/135* (2016.08); *C12R 1/01* (2013.01); *A23V 2002/00* (2013.01)

(58) Field of Classification Search
None
See application file for complete search history.

(56) References Cited

FOREIGN PATENT DOCUMENTS

ES        8701229 A1    6/1985

OTHER PUBLICATIONS

Morin (Polysaccharides: Structural Diversity and Functional Versatility, edited by Severian Dumitriu, CRC Press, May 12, 1998, Chapter 8, "Polysaccharide producing Microorganisms . . . " by Andre Morin, pp. 275-296).*
Van Beek, S., Memoire de fin d'etudes. Institut Superieur Agricole de Beauvais, France, Centre de recherché et de developpement sur les aliments, St. Hyacinthe, Quebec, Canada. 1997, 70 pages. Parts I and II.*
Smitinont et al "Exopolysaccharide-Producing Lactic Acid Bacteria Strains from Traditional Thai Fermented Foods: Isolation, Identification and Exopolysaccharide Characterization" Int J Food Microbiol vol. 51, pp. 105-111, 1999.
Tserovska et al "Identification of Lactic Acid Bacteria Isolated from Katyk, Goat's Milk and Cheese" Journal of Culture Collections vol. 3, pp. 48-52, 2000.
Duenas et al "Exopolysaccharide Production by Pediococcus Damnosus 2.6 in a Semidefined Medium Under Different Growth Conditions" Int J Food Microbiol vol. 87, pp. 113-120, 2003.
Savadogo et al "Identification of Exopolysasccharides-Producing Lactic Acid Bacteria from Burkina Faso Fermented Milk Samples" African Journal of Biotechnology vol. 3, pp. 189-194, 2004.
Van Der Meulen et al "Screening of Lactic Acid Bacteria Isolates from Dairy and Cereal Products for Exopolysaccharide Production and Genes Involved" Int J Food Microbiol vol. 118, pp. 250-258, 2007.

* cited by examiner

*Primary Examiner* — Irene Marx
(74) *Attorney, Agent, or Firm* — Cesari and McKenna, LLP

(57) ABSTRACT

Disclosed herein is an isolated *Pediococcus acidilactici* 05B0111 capable of producing an exopolysaccharide. The *Pediococcus acidilactici* 05B0111 is deposited in Biosource Collection and Research Center (BCRC) of Food Industry Research and Development Institute (FIRDI) under an accession number BCRC 910420 and deposited in Deutsche Sammlung von Mikroorganismen und Zellkulturen GmbH (DSMZ) under an accession number DSM 22345. A method of producing an exopolysaccharide is also disclosed. The method involves cultivating an isolated *Pediococcus acidilactici* in a suitable medium under condition such that the exopolysaccharide is formed. A pharmaceutical composition including the aforementioned *Pediococcus acidilactici* 05B0111 and a food product including the aforementioned *Pediococcus acidilactici* 05B0111 are disclosed as well.

5 Claims, 4 Drawing Sheets

AGTTTGATCCTGGCTCAGGATGAACGCTGGCGACGTGCCTAATACATGC
AAGTCGAACGAACTTCCGTTAATTGATTATGACGTGCTTGCACTGATGA
GATTTTAACACGAAGTGAGTGGCGGACGGGTGAGTAACACGTGGGTAAC
CTGCCCAGAAGCAGGGGATAACACCTGGAAACAGATGCTAATACCGTAT
AACAGAGAAAACCGCCTGGTTTTCTTTTAAAAGATGGCTCTGCTATCAC
TTCTGGATGGACCCGCGGCGCATTAGCTAGTTGGTGAGGTAACGGCTCA
CCAAGGCGATGATGCGTAGCCGACCTGAGAGGGTAATCGGCCACATTGG
GACTGAGACACGGCCCAGACTCCTACGGGAGGCAGCAGTAGGGAATCTT
CCACAATGGACGCAAGTCTGATGGAGCAACGCCGCGTGAGTGAAGAAGG
GTTTCGGCTCGTAAAGCTCTGTTGTTAAAGAAGAACGTGGGTGAGAGTA
ACTGTTCACCCAGTGACGGTATT (SEQ ID NO: 1)

FIG.1

ISOLATED *PEDIOCOCCUS ACIDILACTICI* 05B0111 AND METHOD OF PRODUCING EXOPOLYSACCHARIDE

CROSS-REFERENCE TO RELATED APPLICATIONS

The present application is a divisional of commonly assigned U.S. patent application Ser. No. 12/818,316, filed on Jun. 18, 2010, now abandoned, which claims the priority of Taiwanese Application No. 098134914, filed on Oct. 15, 2009. Both prior applications are hereby incorporated by reference in their entirety.

BACKGROUND OF THE INVENTION

Field of the Invention

This invention relates to an isolated *Pediococcus acidilactici* 05B0111 having high exopolysaccharide-producing ability. The *Pediococcus acidilactici* 05B0111 was deposited in Biosource Collection and Research Center (BCRC) of Food Industry Research and Development Institute (FIRDI) under accession number BCRC 910420 and deposited under the Budapest Treaty on the International Recognition of the Deposit of Microorganisms for the purpose of Patent Procedure on Mar. 5, 2009 with the International Patent Organism Depositary Deutsche Sammlung von Mikroorganismen and Zellkulturen GmbH (DSMZ), Inhoffenstr. 713, D-38124 Braunschweig, Germany under accession number DSM 22345. This invention also relates to a method of producing an exopolysaccharide, which comprises cultivating an isolated *Pediococcus acidilactici* in a suitable medium under condition such that the exopolysaccharide is formed. This invention also relates to a pharmaceutical composition containing the isolated *Pediococcus acidilactici* 05B0111 and to a food product containing the isolated *Pediococcus acidilactici* 05B0111.

Background Information

Exopolysaccharides (EPS) or extracellular polysaccharides (EPS) are macromolecules produced by microorganisms and secreted outside the cell wall of the microorganisms. EPS are generally classified into (1) capsular EPS that form a slime layer loosely attached to a cell surface and (2) unattached EPS that can be secreted to an environment.

Lactic acid bacteria (LAB) are generally recognized as safe (GRAS), and are widely used probiotics. A number of LAB are able to produce EPS. Most of EPS-producing LAB belong to the genus *Streptococcus*, the genus *Lactobacillus*, the genus *Lactococcus*, the genus *Leuconostoc*, or the genus *Pediococcus* (Petronella J. Looijesteijn et al. (1999), *Applied and Environmental Microbiology*, 65:5003-5008; T. Smitinont et al. (1999), *International Journal of Food Microbiology*, 51:105-111 Patricia Ruas-Madiedo et al. (2007), *Applied and Environmental Microbiology*, 73:4385-4388). In addition, some strains belonging to the genus *Bifidobacterium* are also shown to have the ability to produce EPS (P. Ruas-Madiedo and C. G. de los Reyes-Gavilan (2005), *J. Dairy Sci.*, 88:843-856).

Generally speaking, EPS generated by LAB can be categorized as homopolysaccharides (Ho PS) and heteropolysaccharides (He PS). Ho PS are composed of a single type of monosaccharide. Examples of HoPS include α-glucans (e.g., dextran), β-glucans, and fructans (e.g., levan-type and inulin-type fructans). HePS are composed of repeating units that include different mono saccharides. The repeating units of HePS are normally composed of 3-8 monosaccharides, and mostly include D-glucose, D-galactose, and L-rhamnose. In a few cases, He PS include N-acetylglucosamine, N-acetylgalactosamine, fucose, glucuronic acid, and non-carbohydrate substituents (e.g., phosphate, acetyl group, and glycerol).

EPS produced by LAB are capable of enabling food to have special rheological properties and texture, thereby frequently serving as viscosifiers, stabilizer, emulsifiers, and gelling agents in the food industry. Additionally, many good effects of EPS produced by LAB on health of hosts have been discovered, for example, reduction in cholesterol, modulation of immune activity, antitumor, etc. Since EPS produced by LAB are beneficial to bioactivity, the same has been widely used.

However, EPS produced by bacteria are usually unstable, and yield of the same is normally very low. Since EPS is in great demand, various factors affecting productivity of EPS of LAB have been investigated so as to develop a new cultivation technology for increasing yield of EPS. Petronella J. Looijesteijn et al. mention that strains, culture conditions, and medium composition influence the amount of microbial EPS produced by a certain species, and that a type of a carbon source strongly affects productivity of EPS and may influence composition of EPS as well. Petronella J. Looijesteijn et al. further state that *Lactobacillus delbrueckii* subsp. *bulgaricus* NCFB 2772 generates three times more EPS using glucose than using fructose as a carbon source, and that yields of EPS produced by *Lactobacillus casei* CG11, *Lactobacillus rhamnosus* C83, and *Streptococcus sali vari us* subsp. *Thermophilus* are obviously affected by a carbon source (Petronella J. Looijesteijn et al. (1999), supra).

P. Ruas-Madiedo and C. G. de los Reyes-Gavilan mention that production of EPS by *Lactobacillus casei* CRL87 is 1.7-fold higher in galactose than in glucose, and that *Lactococcus lactis* subsp. *Cremoris* B40 produces larger amounts of EPS in glucose than in fructose (P. Ruas-Madiedo and C. G. de los Reyes-Gavilan (2005), supra). T. Smitinont et al. have reported that two *Pediococcus pentosaceus* strains (AP-1 and AP-3) isolated from traditional Thai food are capable of producing EPS in high yield, and that in liquid media containing 2% sucrose as a carbon source, AP-1 and AP-3 strains are able to respectively produce 6.0 g/L EPS and 2.5 g/L EPS (T. Smitinont et al. (1999), supra).

In addition, among known species belonging to the genus *Pediococcus*, *Pediococcus damnosus*, *Pediococcusparvulus*, and *Pediococcus pentosaceus* are able to produce EPS (Mai to Duenas et al. (2003), *International Journal of Food Microbiology*, 87:113-120; S. Velasco et al. (2006), *International Journal of Food Microbiology*, 111:252-258; T. Smi tinont et al. (1999), supra). However, the applicants indicate that none of literatures or prior art has disclosed the exopolysaccharide-producing ability of *Pediococcus acidilactici* and applications thereof.

During research, the applicants found that *Pediococcus acidilactici* has exopolysaccharide-producing ability. Particularly, the applicants have screened a *Pediococcus acidilactici* isolate, which is phylogenetically different from the published *Pediococcus* strains, from fermented food products. The *Pediococcus acidilactici* isolate has great exopolysaccharide-producing ability, thereby being expected to generate a large number of EPS.

SUMMARY OF THE INVENTION

Therefore, according to a first aspect, this invention provides an isolated *Pediococcus acidilactici* 05B0111 capable of producing an exopolysaccharide. The *Pediococcus acidilactici* 05B0111 is deposited in Biosource Collection and Research Center (BCRC) of Food Industry Research and Development Institute (FIRDI) under an accession number BCRC 910420 and deposited in Deutsche Sammlung von Mikroorganismen and Zellkulturen GmbH (DSMZ) under an accession number DSM 22345.

According to a second aspect, this invention provides a method of producing an exopolysaccharide, which comprises cultivating an isolated *Pediococcus acidilactici* in a suitable medium under condition such that the exopolysaccharide is formed.

According to a third aspect, this invention provides a pharmaceutical composition comprising the aforementioned isolated *Pediococcus acidilactici* 05B0111.

According to a fourth aspect, this invention provides a food product comprising the aforementioned isolated *Pediococcus acidilactici* 05B0111.

BRIEF DESCRIPTION OF THE DRAWINGS

The above and other features and advantages of the present invention will become apparent in the following detailed description of the preferred embodiments with reference to the accompanying drawings, of which:

FIG. 1 shows a full-length nucleotide sequence of 16S rDNA of *Pediococcus acidilactici* 05B0111 according to this invention;

DETAILED DESCRIPTION

Figure 2:
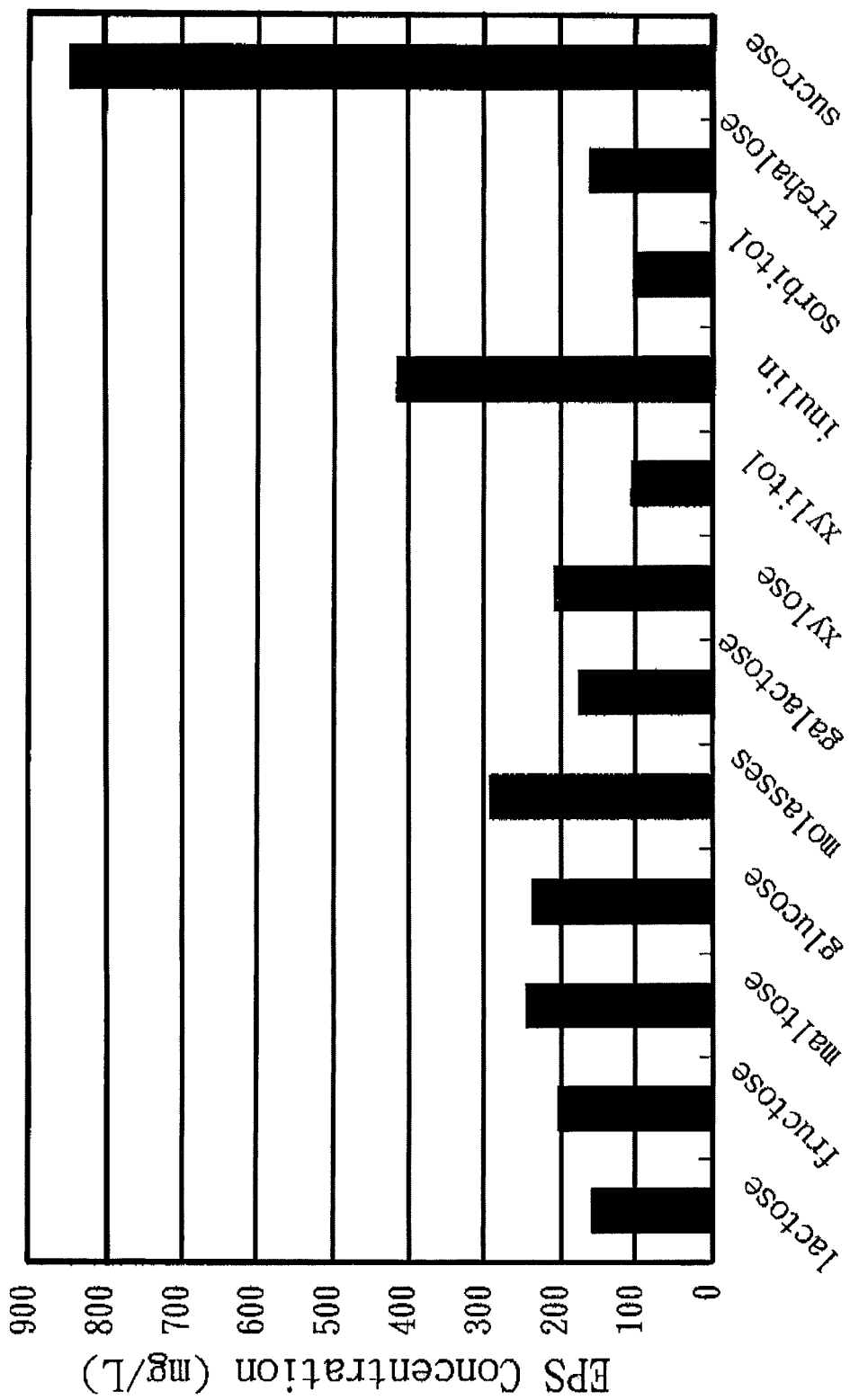
FIG. 2 is a bar diagram showing effects of different carbohydrates on exopolysaccharide-producing ability of *Pediococcus acidilactici* 05B0111 according to this invention.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this invention belongs.

Lactic acid bacteria (LAB) are generally recognized as safe (GRAS), and are widely used probiotics. Many beneficial effects of LAB on health of hosts have been verified. Exopolysaccharides produced by LAB can be widely used. In order to massively produce exopolysaccharides, the applicants have attempted to look for a LAB isolate having high exopolysachharide-producing ability from various LAB.

Accordingly, the applicants preliminarily screened 26 LAB isolates capable of producing exopolysaccharides from fermented food products available in the market. The 26 LAB isolates were subjected to 16S rDNA sequence analysis, and the results show that 5 LAB isolates out of the 26 LAB isolates phylogenetically belong to *Pediococcus acidilactici*. Particularly, by virtue of evaluation of exopolysaccharide-producing ability and phylogenetic novelty, the applicants found that among the aforementioned 5 LAB isolates, *Pediococcus acidilactici* 05B0111 has the best exopolysaccharide-producing ability and is regarded as a novel LAB isolate. On Feb. 10, 2009, *Pediococcus acidilactici* 05B0111 was deposited in Biosource Collection and Research Center (BCRC) of Food Industry Research and Development Institute (FIRDI) under an accession number BCRC 910420. Furthermore, on Mar. 5, 2009, *Pediococcus acidilactici* 05B0111 was deposited in Deutsche Sammlung von Mikroorganismen and Zellkulturen GmbH (DSMZ) under an accession number DSM 22345 so as to meet the requirement of the Budapest Treaty.

Accordingly, this invention provides a method of producing an exopolysaccharide, which comprises cultivating an isolated *Pediococcus acidilactici* in a suitable medium under condition such that the exopolysaccharide is formed. Preferably, the isolated *Pediococcus acidilactici* cultivated in the method is the isolated *Pediococcus acidilactici* 05B0111. In a preferred embodiment of this invention, the resultant exopolysaccharide is purified.

As used herein, the term "cultivation", the term "culturing", and the term "fermentation" can be interchangeably used.

According to this invention, the medium suitable to cultivate *Pediococcus acidilactici* 05B0111 can be a synthetic medium or an edible material. Examples of the synthetic medium suitable for the present invention include, but are not limited to, MRS broth. Examples of the edible material suitable for the present invention include, but are not limited to, a fluid milk product (e.g., milk and concentrated milk), milk powder, fruit juice, soybean milk, vegetable-fruit juice, health food, animal feed, an agricultural product, a livestock product, an aquatic product, and a functional ingredient. In a preferred embodiment of this invention, the edible material used as the medium is milk. In another preferred embodiment of this invention, the edible material used as the medium is orange juice. In yet another preferred embodiment of this invention, the edible material used as the medium is soybean milk.

According to this invention, the suitable medium comprises a carbon source selected from the group consisting of: lactose, fructose, maltose, glucose, molasses, galactose, xylose, xylitol, inulin, sorbitol, trehalose, sucrose, and mixtures thereof. Preferably, the carbon source is selected from the group consisting of: maltose, glucose, molasses, xylose, inulin, sucrose, and mixtures thereof. More preferably, the carbon source is selected from the group consisting of: inulin, sucrose, and mixtures thereof. In the preferred embodiments of this invention, the carbon source is sucrose.

Preferably, before cultivating, the suitable medium has a pH value ranging from 3 to 7. In a preferred embodiment of this invention, before cultivating, the suitable medium has a pH value of 5.

Preferably, the cultivating step for *Pediococcus acidilactici* 05B0111 is conducted at a temperature ranging from 25° C. to 37° C. In a preferred embodiment of this invention, *Pediococcus acidilactici* 05B0111 is cultivated at 30° C.

Isolation and purification of exopolysaccharides, and determination of exopolysaccharide concentration can be performed by virtue of techniques known to a skilled artisan. For example, exopolysaccharides can be isolated and purified using trichloroacetic acid or ethanol. Exopolysaccharide concentration can be determined using phenol-sulfuric method (P. Ruas-Madiedo and C. G. de los Reyes-Gavilán (2005), supra).

Exopolysaccharides isolated and purified from culture of *Pediococcus acidilactici* 05B0111 have been used to culture macrophages and have been hence shown to have immunomodulating activity. Moreover, based on other known probiotic properties of exopolysaccharides, the culture of *Pediococcus acidilactici* 05B0111, which contains exopolysaccharides, is expected to be applicable to production of drugs for immune modulation, lowering cholesterol, and antitumor.

Accordingly, this invention provides a pharmaceutical composition comprising the isolated *Pediococcus acidilactici* 05B0111. Preferably, the pharmaceutical composition further comprises the exopolysaccharide obtained from the aforementioned method of producing an exopolysaccharide.

The pharmaceutical composition may be orally administrable and can be formulated into a dosage form of e.g., solution, suspension, emulsion, powder, a tablet, a pill, syrup, lozenge, troche, chewing gum, a capsule, slurry, and an analogue thereof. Preferably, the pharmaceutical composition further comprises a pharmaceutically acceptable carrier.

As used herein, the term "pharmaceutically acceptable carrier" refers to a carrier that is not able to induce an allergic reaction or an undesired effect in a subject when being administered to the same. According to this invention, the pharmaceutically acceptable carrier may include one or more of the following reagents: a solvent, emulsifier, a suspending agent, decomposer, a binding agent, an excipient, a stabilizing agent, a chelating agent, diluent, a gelling agent, preservative, lubricant, and an analogue thereof.

Besides the oral dosage form, the pharmaceutical composition containing the isolated *Pediococcus acidilactici* 05B0111 can also be formulated into a suitable dosage form for topical administration (e.g., percutaneous administration or intranasal administration). Examples of the suitable dosage form for topical administration include, but are not limited to cream, lotion, ointment, nasal spray formulation, aerosol, and dry powder inhaler.

Additionally, this invention provides a food product that comprises an edible material and the isolated *Pediococcus acidilactici* 0580111. Preferably, the food product further comprises the exopolysaccharide obtained from the aforementioned method of producing an exopolysaccharide. Examples of the edible material contained in the food product include, but are not limited to, milk powder, a beverage, confectionery, a candy, a fermented food, animal feeds, a health food, a dietary supplement, jelly, infant formula, salad dressing, mayonnaise, spread, cream, a sauce, a pudding, ice-cream, a bakery product, ketchup, and mustard.

The culture medium of *Pediococcus acidilactici* 05B0111, which contains exopolysaccharides, is expected to be applicable to production of health food and non-prescribed drugs for immune modulation, lowering cholesterol, and antitumor. Regarding the food product of this invention, the edible material thereof can be used as a medium for cultivation of the isolated *Pediococcus acidilactici* 05B0111.

This invention will be further described by way of the following examples. However, it should be understood that the following examples are solely intended for the purpose of illustration and should not be construed as limiting the invention in practice.

EXAMPLES

Experimental Materials:
A. MRS Broth:
  MRS broth to be used in the following examples is commercially available Lactobacilli MRS broth (DIFCO, Cat. No. 0881) that contains 2% glucose as a carbon source.
B. MRS-Carbohydrate Broth:
  MRS-carbohydrate broth to be used in the following examples is formulated mainly according to the recipe of MRS broth, except that a carbohydrate other than glucose is used as a carbon source, and that carbohydrate concentration of the MRS-carbohydrate broth is 10%. For instance, the MRS-sucrose broth contains 10% sucrose instead of 2% glucose.
C. Beverage Containing 10% (v/v) Sucrose:
  Beverages to be used in the following examples are orange juice (pH=3.89)(purchased from Chia Meei Food Indl. Corp.), whole milk (purchased from Kuang Chuan Dairy Co., Ltd.), and soybean milk without sugar (purchased from I-Mei Foods Co., Ltd.).

First, a proper amount of sucrose was dissolved in ddH$_2$O so as to make a sucrose stock solution having a concentration of 50% (v/v), followed by sterilization at 121° C. for 15 minutes. The 50% sucrose stock solution was then cooled down for further use. The orange juice was placed in a water bath of 90° C. for 1 minute for sterilization. Furthermore, each of the whole milk and the soybean milk without sugar was placed in a water bath of 100° C. for 30 minutes for sterilization. The three beverages were cooled down to room temperature. A portion of the orange juice (pH=3.89) was obtained, and pH thereof was adjusted to 5.0 using NaOH.

A proper amount of the 50% sucrose stock solution was added to each of the sterile orange juice (pH=3.89 and pH=5), and to each of the sterile whole milk and the sterile soybean milk without sugar so that orange juice (pH=3.89 and pH=5) containing 10% sucrose, milk containing 10% sucrose, and soybean milk containing 10% sucrose were prepared.

General Experimental Procedures:
A. Isolation and Purification of Exopolysaccharides:
  A test sample having a predetermined volume and 20% trichloroacetic acid having an equivalent volume relative to the test sample were evenly mixed at 200 rpm for 2 hours using a suspension mixer, followed by centrifugation at 3000 rpm for 20 minutes. The resultant supernatant was acquired and was mixed with 95% alcohol (4° C.) having a 2-fold volume relative to the supernatant. The resultant mixture was left at 4° C. overnight and was subsequently centrifuged at 3000 rpm for 20 minutes, followed by removing supernatant. Precipitate was dissolved in ddH$_2$O having an equivalent volume relative to the precipitate, followed by addition of 95% alcohol (4° C.) having a 2-fold volume relative to the resultant solution and overnight storage at 4° C. Centrifugation at 3000 rpm for 20 minutes was performed, and supernatant was removed. Precipitate was freeze-dried so as to obtain gelatinous or membranous exopolysaccharides (EPS) for further use.
B. Determination of EPS Concentration:
  EPS obtained according to the procedures as described in the preceding section, entitled "A. Isolation and purification of exopolysaccharides", were dissolved in ddH$_2$O having a volume equivalent to the predetermined volume of the test sample as mentioned in the preceding section, entitled "A. Isolation and purification of exopolysaccharides". Therefore, an EPS solution was formed. 1 mL of the EPS solution was taken out, followed by sequentially adding 0.5 mL of 5% phenol solution and 2.5 mL of concentrated sulfuric acid, and mixing evenly. The resultant mixture was reacted at room temperature for 10 minutes and was subsequently placed in a water bath of 30° C. for 15 minutes. Finally, an ELISA reader (SpectraMax M2, Molecular Devices) was used to measure absorbance ($OD_{490}$) of the resultant mixture at a wavelength of 490 nm. $OD_{490}$ of the resultant mixture was converted to a concentration (mg/L) according to a correlation curve that was generated beforehand by plotting concentrations (0 mg/L, 20 mg/L, 40 mg/L, 80 mg/L, and 100 mg/L) of EPS standards and respective $OD_{490}$.

Example 1. Screening of Lactic Acid Bacteria Isolates Having EPS-Producing Ability A. Source and Isolation of Test Strains:

Lactic acid bacteria strains were isolated from several fermented food products (such as Chinese pickle, kimchi, Chinese cheese, preserved plum, other preserved food products, etc.) purchased from a traditional market. A proper amount of the selected fermented food product was added in MRS broth, followed by cultivation at 37° C. for 1 to 3 days. Subsequently, the resultant bacteria culture was subjected to 10-fold serial dilution so that $10^1$~$10^7$-fold diluted bacteria culture solutions were formed. 0.2 mL of each of the $10^2$-, $10^3$-, $10^4$-, $10^5$-, $10^6$-, and $10^7$-fold diluted bacteria culture solutions was obtained and was evenly applied onto a MRS agar plate, followed by cultivation at 37° C. for 72 hours. Afterward, based on colonial morphology and the results of microscopic examination, the applicants selected 121 lactic acid bacteria isolates and purified the same several times. Each of the purified lactic acid bacteria isolates was mixed with 20% glycerol. The resultant mixture was placed in a frozen vial and was stored at −80° C. for further use.

B. Preparation of Inoculums of Lactic Acid Bacteria Isolates:

Each of the lactic acid bacteria isolates as obtained from the preceding section, entitled "A. Source and isolation of test strain", was inoculated in 5 mL of MRS broth so that the MRS broth had the final inoculum concentration of 1% (v/v), followed by cultivation at 37° C. for 18 hours. The aforementioned cultivation step was repeated twice so as to activate the lactic acid bacteria isolates. The resultant culture served as inoculums of the lactic acid bacteria isolate in the following examples.

C. Preliminary Screening of Lactic Acid Bacteria Isolates Having EPS-Producing Ability:

The inoculums of each of the 121 lactic acid bacteria isolates, which were obtained from the preceding section entitled "B. Preparation of inoculums of lactic acid bacteria isolates", were inoculated in EPS selection medium (ESM) so that the ESM had a final inoculum concentration of 1% (v/v), followed by cultivation at 37° C. for 72 hours. A proper amount of the resultant culture was taken out to determine the viscosity thereof using a viscometer (model DV-I+, BROOKFIELD, USA).

In addition, a proper amount of the inoculums of each of the 121 lactic acid bacteria isolates, which were obtained from the preceding section entitled "B. Preparation of inoculums of lactic acid bacteria isolates", were applied onto a MRS-sucrose agar plate by virtue of the four-quadrant streak method, followed by cultivation at 37° C. for 5 days. Physical appearance of the colonies was observed by human vision, and the colonies were picked with tips of toothpicks so as to see whether the colonies could produce ropy strands.

When a lactic acid bacteria isolate meets at least one of the two following requirements, the same is considered as a strain capable of producing EPS:

(1) Viscosity is over 150 cp; and
(2) Slime is observed around colonies, or colonies produce ropy strands when the same are picked with tips of toothpicks.

According to the aforementioned requirements and consideration for factors (such as a source of strains and suitability of strains to develop a food product), the applicants preliminarily screened 26 isolates from the 121 lactic acid bacteria isolates and performed 16S rDNA sequence analysis for the 26 isolates so as to determine the species thereof.

D. 16S rDNA Sequence Analysis:

The inoculums of each of the 26 lactic acid bacteria isolates, which were obtained from the preceding section entitled "B. Preparation of inoculums of lactic acid bacteria isolates", were added onto a MRS agar plate and were evenly spread using a L-shaped glass rod, followed by cultivation at 37° C. for 24 hours. Afterward, a small amount of fresh strains were scraped from the MRS agar plate and transferred to 1.5 mL microcentrifuge tube. Genomic DNA of the bacterial strain was extracted using Blood & Tissue Genomic DNA Extraction Miniprep System (Viogene, U.S.A.). Extracted genomic DNA was dissolved in a proper amount of dd$H_2O$. Therefore, 26 samples, each of which includes genomic DNA of a respective one of the 26 lactic acid bacteria isolates, were formed.

The genomic DNA thus obtained was used as a template in a 16S rDNA PCR (polymerase chain reaction) experiment using GeneAmp® PCR system 9700 (Applied Biosystem) and MicroSeq® Full Gene 16S rDNA Bacterial Identification PCR Kit (Applied Biosystem). After the PCR experiment was completed, 1% agarose gel electrophoresis was performed to detect a PCR amplification product of about 500 bps. By virtue of PCR Clean up-M System (Viogene), the detected PCR amplification product was recycled and purified from the gel.

The purified PCR amplification product was subjected to a cycle sequencing experiment using GeneAmp® PCR system 9700 and MicroSeq® Full Gene 16S rDNA Bacterial Identification Sequencing Kit (Applied Biosystem). The cycle sequencing product was subsequently purified using Performa™ DTR Gel Filtration Systems Gel Filtration Cartridges (Edge BioSystems). The thus purified cycle sequencing product was sequenced using 3730 DNA Analyzer (Applied Biosystems), and the resultant 16S rDNA sequence was compared to the database on NCBI website using MicroSeq®ID analysis software (v. 1.40, Applied Biosystems). The result of comparison is shown in Table 1.

TABLE 1

Comparison of 16S rDNA sequence of lactic acid bacteria isolates

| Number of lactic acid bacteria isolate | Species* | Homology (%) |
|---|---|---|
| 05B0001 | (a) *Lactobacillus kimchii* | 99 |
| | (b) *Lactobacillus paralimentarius* | |
| 05B0002 | *Pediococcus* sp. | 99 |
| 05B0003 | *Pediococcus pentosaceus* | 99 |
| 05B0025 | *Lactobacillus fermentum* | 99 |
| 05B0100 | *Lactobacillus plantarum* | 99 |
| 05B0108 | *Pediococcus pentosaceus* | 99 |
| 05B0111 | *Pediococcus acidilactici* | 99 |

TABLE 1-continued

Comparison of 16S rDNA sequence of lactic acid bacteria isolates

| Number of lactic acid bacteria isolate | Species* | Homology (%) |
|---|---|---|
| 05B0114 | (a) *Streptococcus macedonicus* | 99 |
|  | (b) *Streptococcus waius* |  |
| 05B0115 | *Weissella paramesenteroides* | 99 |
| 05B0116 | *Enterococcus faecalis* | 99 |
| 05B0117 | *Lactobacillus gasseri* | 99 |
| 05B0164 | *Pediococcus acidilactici* | 99 |
| 05B0165 | *Pediococcus pentosaceus* | 99 |
| 05B0166 | *Lactobacillus pontis* | 98 |
| 05B0167 | *Pediococcus acidilactici* | 98 |
| 05B0168 | *Pediococcus acidilactici* | 99 |
| 05B0169 | *Lactobacillus plantarum* | 99 |
| 05B0G5-2 | *Lactobacillus brevis* | 99 |
| 05B013-2 | *Lactobacillus plantarum* | 99 |
| 05B017-1 | *Lactobacillus fermentum* | 99 |
| 05B017-2 | *Lactobacillus delbrueckii* subsp. *bulgaricus* | 99 |
| 05B018-1 | *Lactobacillus fermentum* | 99 |
| 05B029-2 | *Lactobacillus plantarum* | 99 |
| 05B033-1 | *Weissella paramesenteroides* | 99 |
| 05B034-2 | *Pediococcus acidilactici* | 98 |
| 05B046-2 | (a) *Lactobacillus amylovorus* |  |
|  | (b) *Lactobacillus kitasatonis* | 99 |
|  | (c) *Lactobacillus sobrius* |  |
|  | (d) *Lactobacillus gallinarum* |  |

*The column "species" indicates a species name (i.e., a scientific name) of a type strain having 16S rDNA sequence that is most homologous to 16S rDNA sequence of the respective isolate of this invention. If more than one species name appears in the aforementioned column, it indicates that the isolate of this invention has 16S rDNA sequence most homologous to 16S rDNA sequence of more than one type strain.

Referring to Table 1, the results of comparison between 16S rDNA sequences show: 13 isolates belong to the genus *Lactobacillus*, 9 isolates belong to the genus *Pediococcus*, 2 isolates belong to the genus *Weissella*, 1 isolate belongs to the genus *Streptococcus*, and 1 isolate belongs to the genus *Enterococcus*. Particularly, the applicants have noticed that among the 9 isolates belonging to the genus *Pediococcus*, 5 isolates (numbers thereof are 05B0111, 05B0164, 05B0167, 05B0168, and 05B034-2) are *Pediococcus acidilactici*. None of the previous literatures and prior art have disclosed that *Pediococcus acidilactici* has EPS-producing ability.

In order to massively produce EPS, the applicants decided to further screen strains having great EPS-producing ability. Thus, the 26 lactic acid bacteria isolates were subjected to the following experiments.

E. Screening of Lactic Acid Bacteria Isolates Having Great EPS-Producing Ability:

The inoculums of each of the 26 lactic acid bacteria isolates as obtained from the preceding section, entitled "C. Preliminary screening of lactic acid bacteria isolates having EPS-producing ability", were inoculated in 15 mL of MRS-sucrose broth so that the MRS-sucrose broth had a final inoculum concentration of 1% (v/v), followed by cultivation at 37° C. for 72 hours. Isolation and purification of EPS in the resultant culture, and determination of EPS concentration of the resultant culture were performed according to the procedures as described in the sections, entitled "A. Isolation and purification of exopolysaccharides" and "B. Determination of EPS concentration", of the General Experimental Procedures.

The results show that the cultures of the 5 *Pediococcus acidilactici* isolates (numbers thereof 05B0111, 05B0164, 05B0167, 05B0168, and 05B034-2) as preliminarily identified in the preceding section, entitled "D. 16S rDNA sequence analysis", respectively have the following EPS concentrations: 845 mg/L, 11.34 mg/L, 29.51 mg/L, 17.99 mg/L, and 17.74 mg/L. Furthermore, among the remaining 21 lactic acid bacteria isolates, cultures of 4 isolates have EPS concentrations ranging between 60 mg/L and 110 mg/L, and cultures of the rest of the bacteria isolates have EPS concentrations that are ranging between 50 mg/L and 2.89 mg/L. Based on the results of this experiment, the applicants believe that *Pediococcus acidilactici* 05B0111 has the greatest potential for producing EPS. *Pediococcus acidilactici* 05B0111 was further subjected to assessment of phylogenetic novelty.

Example 2. Assessment of Phylogenetic Novelty of *Pediococcus acidilactici* 05B0111

In order to confirm that *Pediococcus acidilactici* 05B0111 as screened in the above Example 1 has phylogeny different from that of the published strains belonging to the genus *Pediococcus*, *Pediococcus acidilactici* 05B0111 was subjected to the following preliminary tests, 16S rDNA sequence analysis, physiological and biochemical tests, and DNA-DNA hybridization analysis.

Experimental Materials and Procedures:

A. Preliminary Tests:

The preliminary tests for *Pediococcus acidilactici* 05B0111 include Gram stain, morphological observation, motility, activity of catalase and oxidase, growth condition under aerobic and anaerobic environments, and ability to produce endospore.

The results show: *Pediococcus acidilactici* 05B0111 is Gram-positive, does not have motility, does not have activity of catalase and oxidase, is able to grow under aerobic and anaerobic environments, and is not able to produce endospore.

B. 16S rDNA Sequence Analysis:

16S rDNA of *Pediococcus acidilactici* 05B0111 was sequenced according to the procedures as described in the section, entitled "D. 16S rDNA sequence analysis", of the above Example 1. The full-length sequence of 16S rDNA of *Pediococcus acidilactici* 05B0111 is shown in FIG. 1, and was compared to the database on NCBI website using MicroSeq®ID analysis software. The comparison shows: the sequence similarity between the full-length sequence (SEQ ID NO:1) of 16S rDNA of *Pediococcus acidilactici* 05B0111 and 16S rDNA sequence of *Pediococcus acidilactici* (Genbank accession number: AJ249535), the sequence similarity between the full-length sequence of 16S rDNA of *Pediococcus acidilactici* 05B0111 and 16S rDNA sequence of *Pediococcus stilesii* (Genbank accession number: AJ973157), and the sequence similarity between the full-length sequence of 16S rDNA of *Pediococcus acidilactici* 05B0111 and 16S rDNA sequence of *Pediococcus claussenii* (Genbank accession number: AF404716) are all over 97%.

C. Physiological and Biochemical Tests:

Temperature tolerance, pH tolerance, NaCl tolerance, and carbohydrate fermentation profile of *Pediococcus acidilactici* 05B0111 were tested.

The procedures of the tests for temperature tolerance, pH tolerance, and NaCl tolerance were slightly modified according to the procedures as described by Charles M. A. P. Franz et al. (Charles M. A. P. Franz et al. (2006), *International Journal of Systematic and Evolutionary Microbiology*, 56:329-333). In a nutshell, a proper amount of the inoculums of *Pediococcus acidilactici* 05B0111, which were prepared in the section entitled "B. Preparation of inoculums of lactic acid bacteria isolates" of the above Example 1, were added onto a MRS agar plate and were evenly spread using a L-shaped glass rod, followed by cultivation at 37° C. for 5 days. Afterward, growth condition of *Pediococcus acidilactici* 05B0111 on the MRS agar plate was observed.

Carbohydrate fermentation profile was tested using API 50 CHL identification system (bioMérieux) and the manual guide thereof. The following carbohydrates were tested: arabinose, galactose, lactose, maltose, ribose, xylose, glycerol, potassium gluconate, potassium 2-keto gluconate, and trehalose.

In addition, due to the results of the section, entitled "B. 16S rDNA sequence analysis", of the Example 2, the applicants used three *Pediococcus* type strains purchased from BCRC of FIRDI as comparative strains to contrast with *Pediococcus acidilactici* 05B0111. The three *Pediococcus* type strains are as follows:

(1) *Pediococcus acidilactici* BCRC 17599$^T$ (corresponding to DSM 20284$^T$) isolated from barley,
(2) *Pediococcus claussenii* BCRC 17600$^T$ (corresponding to DSM 14800$^T$, ATCC BAA-344$^T$, and KCTC 3811$^T$) isolated from spoiled beer, and
(3) *Pediococcus stilesii* BCRC 17601$^T$ (corresponding to DSM 18001$^T$, CCUG 51290$^T$, and LMG 23082$^T$) isolated from white maize grains.

Temperature tolerance, pH tolerance, NaCl tolerance, and carbohydrate fermentation profile regarding *Pediococcus acidilactici* 05B0111 and the three *Pediococcus* type strains are shown in Table 2.

TABLE 2

Physiological and biochemical tests for *Pediococcus acidilactici* 05B0111 and three *Pediococcus* type strains

| Test | | Pediococcus acidilactici 05B0111 | Pediococcus acidilactici BCRC 17599$^T$ | Pediococcus claussenii BCRC 17600$^T$ | Pediococcus stilesii BCRC 17601$^T$ |
|---|---|---|---|---|---|
| pH tolerance* | pH 4.2 | + | + | + | + |
| | pH 7.0 | + | + | + | + |
| | pH 8.0 | + | + | + | + |
| | pH 9.0 | + | − | − | + |
| Temperature tolerance* | 35° C. | + | + | + | + |
| | 40° C. | + | + | + | + |
| | 45° C. | + | − | − | + |
| | 50° C. | + | − | − | − |
| NaCl Tolerance* | 4% NaCl | + | + | + | + |
| | 5% NaCl | + | + | + | + |
| | 6% NaCl | + | + | − | + |
| | 8% NaCl | + | + | − | + |
| | 10% NaCl | − | + | − | − |
| Carbohydrate fermentation profile** | Arabinose | − | + | − | − |
| | Galactose | + | + | − | + |
| | Lactose | − | − | − | − |
| | Maltose | − | − | + | + |
| | Ribose | + | + | + | + |
| | Xylose | − | + | − | − |
| | Glycerol | − | − | − | + |
| | Potassium gluconate | − | − | − | + |
| | Potassium 2-keto gluconate | − | − | − | + |
| | Trehalose | + | + | + | − |

*Regarding results of the tests for pH tolerance, temperature tolerance, and NaCl tolerance, "+" indicates that the test strain is able to grow on the MRS agar plate with the respective condition, and "−" indicates that the test strain is not able to grow on the MRS agar plate with the respective condition.
**Regarding results of the tests for carbohydrate fermentation profile, "+" indicates that the test strain is capable of using the respective carbohydrate to perform fermentation and produce acid, and "−" indicates that the test strain is not capable of using the respective carbohydrate to perform fermentation.

Based on the results shown in Table 2, the applicants believe that the physiological and biochemical characteristics of *Pediococcus acidilactici* 05B0111 are generally conformable to those of strains belonging to *Pediococcus*, and are similar to those of *Pediococcus acidilactici* BCRC 17599$^T$, *Pediococcus claussenii* BCRC 17600$^T$, and *Pediococcus stilesii* BCRC 17601$^T$.

D. DNA-DNA Hybridization Analysis:

In order to further confirm the species of *Pediococcus acidilactici* 05B0111, the applicants prepared genomic DNA samples of *Pediococcus acidilactici* 05B0111, *Pediococcus acidilactici* BCRC 17599$^T$, *Pediococcus claussenii* BCRC 17600$^T$, and *Pediococcus stilesii* BCRC 17601$^T$ according to the procedures as described in the section, entitled "D. 16S rDNA sequence analysis", of the above Example 1. The applicants conducted DNA-DNA hybridization according to the procedures as described by Takayuki Ezaki et al. (Takayuki Ezaki et al. (1989), *International Journal of Systematic Bacteriology*, 39:224-229). First, each of the genomic DNA samples was subjected to heat-denaturing, followed by mixing with phosphate buffered saline (PBS) containing 0.1 M MgCl$_2$ so as to make a DNA solution having a concentration of 20 μg/mL The DNA solution of *Pediococcus acidilactici* 05B0111 was designated as the 05B0111 group, and the DNA solutions of *Pediococcus acidilactici* BCRC 17599$^T$, *Pediococcus claussenii* BCRC 17600$^T$, and *Pediococcus stilesii* BCRC 17601$^T$ were designated as the type strain groups. Furthermore, a DNA solution (Merck, Cat. No. 2618) of calf *thymus* served as the negative control group. 100 μL of the DNA solution of each group was added into a respective well of a 96-well plate, followed by cultivation at 37° C. for 1 hour. Each of the DNA solutions was removed from the respective well. The wells were rinsed using PBS containing 0.1 M MgCl$_2$. The 96-well plate was dried at 60° C. overnight.

In addition, 5 μL of photobiotin and 5 μL of the heat-denatured genomic DNA sample (1 μg/μL, in distilled water) of *Pediococcus acidilactici* 05B0111 were added into a microcentrifuge tube and evenly mixed, followed by illumination for 15 minutes by a sunlamp (500 W). Free photobiotin was removed by virtue of 2-butanol extraction. Consequently, biotinylated DNA was formed and was kept for further use.

The 96-well plate that was dried overnight was obtained. 200 μL of a prehybridization solution (containing 2×SSC, 5×Denhardt solution, denatured salmon sperm DNA (200 μg/mL), and 50% formamide) was added into each of the wells coated with the respective DNA solutions, followed by cultivation at 37° C. for 1 hour. The liquid in each of the wells was removed. Subsequently, 100 μL of a hybridization solution (containing 2×SSC, 5×Denhardt solution, 3% dextran sulfate, 50% formamide, denatured salmon DNA (50 μg/mL), and 50 ng of the biotinylated DNA) was added into each of the wells, followed by hybridization reaction at 42° C. for 1 hour. The liquid in each of the wells was removed. Each of the wells was washed four times using 300 μL of 2×SSC buffer solution, followed by adding 100 μL of streptavidin-beta-D-galactosidase solution (10 ng/mL, in PBS containing 0.5% bovine serum albumin and 0.1% Triton X-100). The resultant mixtures were allowed to react at 37° C. for 30 minutes.

Afterward, the liquid in each of the wells was removed, and each of the wells was rinsed twice with PBS containing 0.1% Triton X-100. 100 μL of 4-methylumbelliferyl-beta-D-galactopyrano side (3×10$^{-4}$ M, in PBS) was added into each of the wells. The resultant mixtures were allowed to react at 37° C. for 10 minutes. Fluorescence intensity of the resultant mixture in each of the wells was measured at 360 nm (excitation wavelength) and 450 nm (emission wavelength) using Fluoroskan II microplate fluorometer (Labsystems).

DNA relatedness between *Pediococcus acidilactici* 05B0111 and *Pediococcus acidilactici* BCRC 17599$^T$, DNA relatedness between *Pediococcus acidilactici* 05B0111 and *Pediococcus claussenii* BCRC 17600$^T$, and DNA relatedness between *Pediococcus acidilactici* 05B0111 and *Pediococcus stilesii* BCRC 17601$^T$ were calculated by substituting the fluorescence intensity as measured in this section into the following formula:

DNA relatedness (%)=[(A−C)/(B−C)]×100 where:
  A=fluorescence intensity of the type strain group
  B=fluorescence intensity of the 05B0111 group
  C=fluorescence intensity of the negative control group The results show that DNA relatedness between the genomic DNAs of *Pediococcus acidilactici* 05B0111 and *Pediococcus acidilactici* BCRC 17599$^T$, DNA relatedness between the genomic DNAs of *Pediococcus acidilactici* 05B0111 and *Pediococcus claussenii* BCRC 17600$^T$, and DNA relatedness between the genomic DNAs of *Pediococcus acidilactici* 05B0111 and *Pediococcus stilesii* BCRC 17601$^T$ are 75.5%, 21.1%, and 4.9%, respectively. Based on the results, the applicants confirmed that the isolate 05B0111 is *Pediococcus acidilactici*.

Based on the results of the aforementioned tests and analysis, Bergey's Manual of Determinative Bacteriology (Holt et al. (1994), *Bergey's Manual of Determinative Bacteriology*, 9$^{th}$ edition, Williams & Wilkins), and the microbiology literatures (e.g., Franz et al. (2006), *International Journal of Systematic and Evolutionary Microbiology*, 56:329-333), the applicants deem that *Pediococcus acidilactici* 05B0111 of this invention is a novel *Pediococcus acidilactici* isolate.

*Pediococcus acidilactici* 05B0111 of this invention was deposited in BCRC of FIRDI (331 Shih-Pin Road, Hsinchu 300, Taiwan) under the accession number BCRC 910420 on Feb. 10, 2009. *Pediococcus acidilactici* 05B0111 was also deposited in DSMZ under the accession number DSM 22345 on Mar. 5, 2009 so as to meet the requirement of the Budapest Treaty.

Example 3. Acid Tolerance Test and Bile Salt Tolerance Test for *Pediococcus acidilactici* 05B0111

*Pediococcus acidilactici* 05B0111 of this invention was subjected to the following experiments so as to investigate whether the same is able to survive under the strict condition of the digestive tract after being ingested.
Experimental Procedures:
A. Acid Tolerance Test:

A proper amount of the inoculums of *Pediococcus acidilactici* 05B0111, which were obtained from the section entitled "B. Preparation of inoculums of lactic acid bacteria isolates" of the above Example 1, were inoculated into 10 mL of MRS broth, followed by cultivation at 37° C. for 24 hours and centrifugation at 3000 rpm for 10 minutes. The supernatant was then removed, and 1 mL of PBS was added to sufficiently suspend strains. Thus, a suspension was made. 0.5 mL of the suspension was inoculated into each of two PBS solutions (pH=2 and pH=7.2) having a volume of 10 mL, and was sufficiently mixed with the same. The resultant mixture was placed at 37° C. for 2 hours for cultivation. 1 mL of the resultant culture was obtained and was subjected to 10-fold serial dilution using PBS, followed by a spread plate procedure to count the viable bacteria.
B. Bile Salt Tolerance Test:

The inoculums of *Pediococcus acidilactici* 05B0111, which were obtained from the section entitled "B. Preparation of inoculums of lactic acid bacteria isolates" of the above Example 1, were inoculated into each of 10 mL of MRS broth and 10 mL of MRS broth containing 0.3% (v/v) oxgall (DIFCO) so that the MRS broth without oxgall and the MRS broth containing 0.3% oxgall had final inoculum concentrations of 2% (v/v), followed by mixing sufficiently. The resultant mixture was placed at 37° C. for 24 hours for cultivation. 1 mL of the resultant culture was subjected to 10-fold serial dilution using PBS, followed by a spread plate procedure to count the viable bacteria.
Results:

When the PBS solutions having pH 2 and pH 7.2 were used to cultivate *Pediococcus acidilactici* 05B0111 of this invention for 2 hours, the viable bacteria counts are respectively 9.05 log CFU/mL and 9.40 log CFU/mL. In addition, when the MRS broth without oxgall and the MRS broth containing 0.3% (v/v) oxgall were used to cultivate *Pediococcus acidilactici* 0580111 of this invention for 24 hours, the viable bacteria counts are respectively 9.07 log CFU/mL and 8.40 log CFU/mL. The results prove that *Pediococcus acidilactici* 05B0111 of this invention is able to tolerate acid and bile salt, and is hence capable of tolerating the environment of the human digestive tract after being ingested.

Example 4. Effects of Different Cultivation Conditions on EPS-Producing Ability of *Pediococcus acidilactici* 05B0111

A. Effects of Carbohydrates on EPS-Producing Ability of *Pediococcus acidilactici* 05B0111:

12 kinds of carbohydrates (i.e., lactose, fructose, maltose, glucose, molasses, galactose, xylose, xylitol, inulin, sorbitol, trehalose, and sucrose) were used as carbon sources so as to investigate effects thereof on EPS-producing ability of *Pediococcus acidilactici* 05B0111.

The inoculums of *Pediococcus acidilactici* 05B0111, which were obtained in the section entitled "B. Preparation of inoculums of lactic acid bacteria isolates" of the above Example 1, were inoculated into each of 12 kinds of MRS-carbohydrate broth (each has 15 mL) so that each of the 12 kinds of MRS-carbohydrate broth had a final inoculum concentration of 1% (v/v), followed by cultivation at 37° C. for 72 hours. Isolation and purification of EPS in the resultant culture, and determination of EPS concentration of the resultant culture were conducted according to the procedures as described in the sections, entitled "A. Isolation and purification of exopolysaccharides" and "B. Determination of EPS concentration", of the above General Experimental Procedures. The results are shown in FIG. 2.

Referring to FIG. 2, EPS-producing ability of *Pediococcus acidilactici* 05B0111 varies with the different carbon sources. Particularly, compared to other carbohydrates, EPS concentration is the highest (about 850 mg/L) when sucrose serves as a carbon source. The results indicate that when *Pediococcus acidilactici* 05B0111 of this invention utilizes sucrose as a carbon source for growth and as an energy source, the same is able to produce a large number of EPS.
B. Effects of Temperatures on EPS-Producing Ability of *Pediococcus acidilactici* 05B0111:

Effects of different cultivation temperatures on EPS-producing ability of *Pediococcus acidilactici* 05B10111 were examined when sucrose served as a carbon source.

The inoculums of *Pediococcus acidilactici* 05B0111, which were obtained in the section entitled "B. Preparation of inoculums of lactic acid bacteria isolates" of the above Example 1, were inoculated into each of two portions (each had 5 L) of orange juice containing 10% sucrose so that each of the two portions of the orange juice had a final inoculum concentration of 4% (v/v), followed by placing the two portions of the orange juice respectively at 30° C. and 37° C. for cultivation. At 8 hrs and 72 hrs, a part of the resultant culture was obtained; and isolation and purification of EPS in the resultant culture, and determination of EPS concentration of the resultant culture were conducted according to the procedures as described in the sections, entitled "A. Isolation and purification of exopolysaccharides" and "B. Determination of EPS concentration", of the above General Experimental Procedures. The results are shown in FIG. 3.

Figure 3:
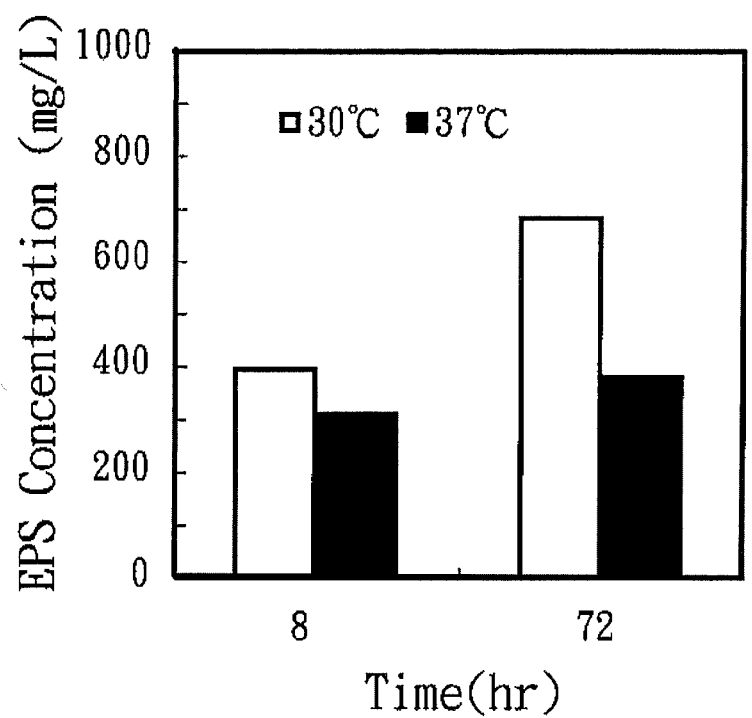
FIG. 3 is a bar diagram showing exopolysaccharide concentration in orange juice containing 10% sucrose at different time points (8 hrs and 72 hrs) of cultivation. The orange juice containing 10% sucrose was inoculated with *Pediococcus acidilactici* 05B0111 according to this invention, followed by cultivation at a respective one of 30° C. and 37° C.

Referring to FIG. 3, at 8 hrs and 72 hrs, EPS concentration of the culture cultivated at 30° C. is higher than that of the culture cultivated at 37° C. The results show that when *Pediococcus acidilactici* 05B0111 of this invention uses sucrose as a carbon source and is cultivated at 30° C., the same has better EPS-producing ability.

C. Effects of Initial pH Values on EPS-Producing Ability of *Pediococcus acidilactici* 05B0111:

Effects of different initial pH values on EPS-producing ability of *Pediococcus acidilactici* 05B0111 were investigated when sucrose served as a carbon source and cultivation was conducted at 30° C.

The inoculums of *Pediococcus acidilactici* 05B0111, which were obtained in the section entitled "B. Preparation of inoculums of lactic acid bacteria isolates" of the above Example 1, were inoculated into 80 mL of each of the two portions of the orange juice (both contained 10% sucrose and respectively had initial pH values of 3.89 and 5.0) so that each of the two portions of the orange juice had a final inoculum concentration of 4% (v/v), followed by placing at 30° C. for 72 hours for cultivation. Isolation and purification of EPS in the resultant culture, and determination of EPS concentration of the resultant culture were performed according to the procedures as described in the sections, entitled "A. Isolation and purification of exopolysaccharides" and "B. Determination of EPS concentration", of the above General Experimental Procedures.

As a result, EPS concentration of the culture cultivated using the medium with the initial pH value of 3.89 is 677.33 mg/L, and EPS concentration of the culture cultivated using the medium with the initial pH value of 5.0 is 1154 mg/L. The results prove that when *Pediococcus acidilactici* 05B0111 of this invention utilizes sucrose as a carbon source and is cultivated at 30° C. using a medium with an initial pH value of 5.0, the same has better EPS-producing ability.

Example 5. Evaluation of EPS-Producing Ability of *Pediococcus acidilactici* 05B0111 in Different Beverages In order to examine how EPS concentration of beverages containing 10% (v/v) sucrose is affected by addition of *Pediococcus acidilactici* 05B0111 of this invention, first, isolation and purification of EPS, and determination of EPS concentration were performed according to the procedures as described in the sections, entitled "A. Isolation and purification of exopolysaccharides" and "B. Determination of EPS concentration", of the above General Experimental Procedures for a proper amount of each of the following beverages containing 10% (v/v) sucrose:orange juice, milk, and soybean milk.

Afterward, the inoculums of *Pediococcus acidilactici* 05B0111, which were obtained in the section entitled "B. Preparation of inoculums of lactic acid bacteria isolates" of the above Example 1, were inoculated into each of the orange juice (5 L) containing 10% sucrose, the milk (30 mL) containing 10% sucrose, and the soybean milk (50 mL) containing 10% sucrose so that the orange juice, the milk, and the soybean milk respectively had final inoculum concentrations (v/v) of 4%, 2%, and 2%. The orange juice with the inoculums was placed at 30° C. for 72 hours of cultivation, and the milk with the inoculums and the soybean milk with the inoculums were placed at 37° C. for 72 hours for cultivation. Isolation and purification of EPS in the resultant culture, and determination of EPS concentration of the resultant culture were conducted according to the procedures as described in the sections, entitled "A. Isolation and purification of exopolysaccharides" and "B. Determination of EPS concentration", of the above General Experimental Procedures.

Before inoculation with *Pediococcus acidilactici* 05B0111 of this invention, EPS concentrations of the orange juice containing 10% sucrose, the milk containing 10% sucrose, and the soybean milk containing 10% sucrose are respectively 452 mg/L, 10 mg/L, and 157 mg/L. After the inoculation with *Pediococcus acidilactici* 05B0111 of this invention and cultivation for 72 hours, EPS concentrations of the cultures cultivated using the orange juice, the milk, and the soybean milk are respectively 677 mg/L, 655 mg/L, and 1128 mg/L. The results indicate that *Pediococcus acidilactici* 05B0111 of this invention has EPS-producing ability in different beverages and is able to be widely used in the food industry.

Example 6. Evaluation for Ability of EPS Produced by *Pediococcus acidilactici* 05B0111 to Stimulate Proinflammatory Cytokine Secretion and Nitric Oxide Secretion of Mouse Macrophage Mouse macrophages were cultivated with EPS produced by *Pediococcus acidilactici* 05B0111 of this invention. In this example, Interleukin-6 (IL-6), interleukin-10 (IL-10), monocyte chemoattractant protein-1 (MCP-1), interferon-γ (IFN-γ), tumor necrosis factor-α (TNF-α), and interleukin-12P70 (IL-12p70) were regarded as indices of expression level of proinflammatory cytokines, and nitrite served as an index of level of nitric oxide (NO).

Experimental Materials and Procedures:

A. Source and Cultivation of Macrophage:

13.4 g of Dulbecco's modified Eagle's medium (DMEM) powder (HyClone) and 1.5 g of sodium bicarbonate ($NaHCO_3$) were respectively added into 600 mL of dd$H_2O$ and 300 mL of dd$H_2O$. After sufficient dissolution, the two resultant mixtures were evenly blended together, followed by adjusting pH to 7.2~7.4 by virtue of 1N HCl. Therefore, DMEM medium was prepared. 10% heat inactivated fetal bovine serum (FBS) and 2% glutamine were added into DMEM, followed by filtration using a membrane filter (Millipore) having a pore size of 0.22 μm and storage at 4° C.

In this example, mouse BALB/c macrophage RAW 264.7 (purchased from BCRC of FIRDI, accession number: BCRC 60001) was used. Macrophages RAW 264.7 were placed in a 10 cm Petri dish having DMEM (containing 10% FBS, 4 mM glutamine, and 1.5 g/L sodium bicarbonate, pH=7.2~7.4), and were cultivated in an incubator with culture conditions set at 37° C. and 5% $CO_2$.

When 80~90% of the bottom area of the Petri dish was covered by macrophages RAW 264.7, and cell growth patterns observed using microscope were normal, DMEM was removed from the Petri dish. 3 mL of fresh DMEM was added into the Petri dish. The fresh DMEM in the Petri dish was sucked and discharged using a pipette so as to repeatedly rinse the cells in the bottom of the Petri dish. Thus, the cells were detached from the bottom of the Petri dish, and a suspension was formed. A proper amount of the suspension was added into a new Petri dish containing 10 mL of DMEM, followed by cultivation in an incubator with culture conditions set at 37° C. and 5% $CO_2$.

B. Preparation of EPS Test Solution:

The EPS solution (845 mg/L) produced by *Pediococcus acidilactici* 05B0111, which was obtained in the section entitled "E. Screening of lactic acid bacteria isolates having great EPS-producing ability" of the above Example 1, was diluted using sterile water so that EPS test solutions having final concentrations of 422.5 mg/L, 169 mg/L, and 84.5 mg/L were made. A portion of the original EPS solution (845 mg/L) was used as an EPS test solution as well. All of the EPS test solutions were filtered using a membrane filter having a pore size of 0.22 μm for further use.

C. Evaluation for Ability of EPS Produced by *Pediococcus acidilactici* 05B0111 to Stimulate Proinflammatory Cytokine Secretion of Macrophage RAW 264.7:

Before performing this experiment, macrophages RAW 264.7 subjected to sub-culture according to procedures as described in the preceding section, entitled "A. Source and cultivation of macrophage", were acquired, and cell concentration was adjusted using DMEM. Consequently, a cell suspension having a cell concentration of $8 \times 10^5$ cell/mL was made. 100 of the aforementioned cell, suspension of macrophages RAW 264.7 was added into each well of a 96-well plate, followed by centrifugation at 1000 rpm for 5 minutes. The 96-well plate was then placed in an incubator (37° C., 5% $CO_2$) for 1~2 hours for cultivation. Therefore, macrophages RAW 264.7 were attached to the bottom of each well. Macrophages RAW 264.7 were arranged into 7 groups that include 4 experiment groups, 2 control groups (a positive group and a negative group), and 1 blank group. The 7 groups were added with the following materials: (1) each of the experimental groups 1, 2, 3, 4 was added with 20 μL of the respective one of the EPS test solutions having the concentrations of 84.5 mg/L, 169 mg/L, 422.5 mg/L, and 845 mg/L; (2) the positive control group was added with 20 μL, of lipopolysaccharide (LPS)(10 μg/mL); (3) the negative control group was added with 20 μL of DMEM; and (4) the blank group was added with 20 μL of sterile water.

After cultivation in an incubator (37° C., 5% $CO_2$) for 24 hours, the liquid in each well was obtained so as to conduct enzyme linked immunosorbent assay (ELISA) using mouse TNF-α/TNFSF1A (R&D Systems, Cat. No. DY410). Absorbances ($OD_{450}$) of the 4 experimental groups were measured at a wavelength of 450 nm, and were converted to concentrations (pg/mL) according to a correlation curve that was previously generated by plotting concentrations of TNF-α standards and the respective absorbances ($OD_{450}$). Additionally, a portion of the cell culture of the experimental group 4 and a portion of the cell culture of the blank group were analyzed by virtue of Cytometric Bead Array using Mouse Inflammation Kit (BD, Cat. No. 552364).

D. Evaluation for Ability of EPS Produced by *Pediococcus acidilactici* 05B0111 to Stimulate Nitric Oxide Secretion of Macrophage RAW 264.7:

Macrophages RAW 264.7 subjected to sub-culture according to procedures as described in the preceding section, entitled "A. Source and cultivation of macrophage", were plated in each well ($1 \times 10^5$ cell/well) of a 96-well plate, followed by overnight cultivation at 37° C. Macrophages RAW 264.7 were arranged into four groups including three experiment groups and one positive control group. Each of the three experiment groups (designated as 1%, 5%, and 10% EPS groups) was added with 100 μL of a respective one of three solutions that all contain 100 ng/mL lipopolysaccharide and 1 ng/mL IFN-γ, and that respectively contain 1% (v/v), 5% (v/v), and 10% (v/v) EPS test solutions. The positive control group was added with 100 μL of a solution containing only 100 ng/mL lipopolysaccharide and 1 ng/mL IFN-γ. Cultivation was conducted at 37° C. for 24 hours.

50 μL of the liquid in each of the wells was acquired and was added into a respective well of a new 96-well plate for the following nitric oxide assay (NO assay). 50 μL of sulfanilamide (60 mM) and 50 μL of N-1-naphthylethylenediamine (4 mM) were added into each of the wells of the aforementioned new 96-well plate, followed by shaking for 5 minutes. Absorbance ($OD_{540}$) of the mixture in each of the wells was measured at a wavelength of 540 nm using the ELISA reader. $OD_{540}$ of the mixture was converted to a nitrite concentration according to a correlation curve that was generated beforehand by plotting different known concentrations of sodium nitrite ($NaNO_2$) and the respective absorbances ($OD_{540}$). The nitrite concentration of the positive control group was regarded as 100%, and relative percentage of nitrite concentrations of the three EPS groups was calculated based on the nitrite concentration of the positive control group.

Figure 4:
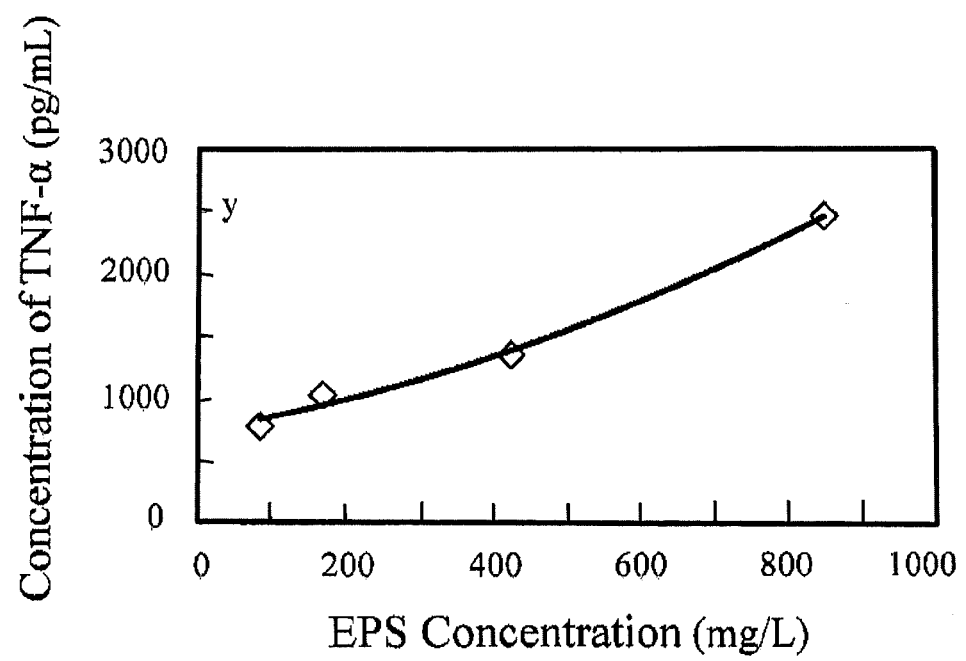
FIG. 4 is a graph showing concentrations of TNF-α secreted by mouse BALB/c macrophages RAW 264.7 at different exopolysaccharide concentrations.

Results:

The results of ELISA in the preceding section, entitled "C. Evaluation for ability of EPS produced by *Pediococcus acidilactici* 05B0111 to stimulate proinflammatory cytokine secretion of macrophage RAW 264.7", are shown in FIG. 4. Referring to FIG. 4, the concentration of TNF-α secreted by macrophages RAW 264.7 increases with the increase of the EPS concentration. The results show that EPS produced by *Pediococcus acidilactici* 05B0111 are capable of stimulating macrophages RAW 264.7 to secrete TNF-α. Namely, EPS produced by *Pediococcus acidilactici* 05B0111 are able to assist in activation of macrophages.

The results of analysis using Cytometric Bead Array are as follows. Regarding the blank group, after macrophages RAW 264.7 were cultured for 24 hours using the sterile water, the concentrations of IL-6, IL-10, MCP-1, TNF, and IL-12p70 were respectively 0 pg/mL, 0 pg/mL, 113 pg/mL, 0 pg/mL, 1362 pg/mL, and 0 pg/mL. Regarding the experimental group 4, after macrophages RAW 264.7 were cultured for 24 hours using the EPS test solution having the concentration of 845 mg/L, the concentrations of IL-6, IL-10, MCP-1, IFN-γ, TNF, and IL-12p70 were respectively 7 pg/mL, 68 pg/mL, 215 pg/mL, 26 pg/mL, 2473 pg/mL, and 4.92 pg/mL. The results indicate: EPS produced by *Pediococcus acidilactici* 05B0111 of this invention can stimulate macrophages RAW 264.7 to secrete TNF, but are not capable of effectively stimulating macrophages RAW 264.7 to secrete IL-6, IL-10, MCP-1, IFN-γ, and IL-12p70.

The results of NO assay are as follows. After 24 hours of culture for macrophages RAW 264.7 using the respective one of the 1%, 5%, and 10% EPS test solutions, relative percentage of nitrite concentration of each of the EPS groups is reduced. The degree of reduction of relative percentage of nitrite concentration tends to be more obvious when EPS concentration increases. Particularly, nitrite concentration of the 10% EPS group is reduced to about 69% of the nitrite concentration of the positive control group. The results prove that EPS produced by *Pediococcus acidilactici* 05B0111 can repress NO secretion of macrophages RAW 264.7 and are hence able to alleviate inflammatory reactions.

TNF-α can be used as an index of activation of macrophages, and proinflammatory cytokines and NO can serve as indices of inflammatory reactions. Therefore, based on the aforementioned results, the applicants believe: EPS produced by *Pediococcus acidilactici* 05B0111 of this invention can activate macrophages, but do not stimulate macrophages to induce inflammatory reactions, thereby being able to modulate immune activity.

Example 7. Evaluation for Ability of EPS Produced by *Pediococcus acidilactici* 05B0111 Cultivated Using Different Carbohydrates as Carbon Sources to Stimulate TNF-α Secretion of Mouse Macrophages Experimental Materials and Procedures:

The inoculums of *Pediococcus acidilactici* 05B0111, which were obtained in the section entitled "13. Preparation of inoculums of lactic acid bacteria isolates" of the above Example 1, were inoculated into each of 15 mL of MRS broth (containing 10% glucose), 15 mL of MRS-sucrose broth, and 15 mL of MRS-maltose broth so that each of the MRS broth (designated as the glucose group), the MRS-sucrose broth (designated as the sucrose group), and the MRS-maltose broth (designated as the maltose broth) had a final inoculum concentration of 1% (v/v). Cultivation was then conducted at 37° C. for 72 hours. Isolation and purification of EPS in the resultant culture, and determination of EPS concentration of the resultant culture were performed according to the procedures as described in the sections, entitled "A. Isolation and purification of exopolysaccharides" and "B. Determination of EPS concentration", of the Qeneral Experimental Procedures. The purified EPS were dissolved in ddH₂O, followed by 2-fold, 5-fold, and 10-fold dilution using sterile water. Therefore, EPS test solutions having different concentrations were prepared. According to the procedures as described in the section, entitled "C. Evaluation for ability of EPS produced by *Pediococcus acidilactici* 05B0111 to stimulate proinflammatory cytokine secretion of macrophage RAW 264.7", of the above Example 6, the EPS test solutions having different concentrations were used to stimulate macrophages RAW 264.7 to secrete TNF-α, and the concentration of TNF-α secreted by macrophages RAW 264.7 was measured. Macrophages RAW 264.7 that were cultured with sterile water served as the blank group.

Results:

The results are shown in Table 3.

TABLE 3

Evaluation for ability of EPS produced by *Pediococcus acidilactici* 05B0111 cultivated using different carbohydrates as carbon sources to stimulate TNF-α secretion of macrophages RAW 264.7

| Group | EPS test solution Concentration(mg/L) | Concentration of TNF-α (pg/mL) |
|---|---|---|
| Glucose | 233.20 | 5145.04 |
|  | 116.60 | 1081.73 |
|  | 46.64 | 234.64 |
|  | 23.32 | 92.74 |
| Sucrose | 845.11 | 2473.00 |
|  | 422.56 | 1358.94 |
|  | 169.02 | 1039.80 |
|  | 84.51 | 784.38 |
| Maltose | 242.80 | 3810.41 |
|  | 121.40 | 892.49 |
|  | 48.56 | 239.42 |
|  | 24.28 | 74.32 |
| Blank | 0 | 502 |

Referring to Table 3, EPS produced by *Pediococcus acidilactici* 05B0111 using glucose, sucrose, and maltose as carbon sources are all capable of stimulating macrophages RAW 264.7 to secrete TNF-α, and the concentration of TNF-α secreted by macrophages RAW 264.7 increases with the increase of EPS concentration. In addition, compared to the blank group, EPS of the glucose group, the sucrose group, and the maltose group have different abilities to stimulate TNF-α secretion of macrophages RAW 264.7 under the different EPS concentrations. The applicants deduce: molecular weight, structure, and degree of branching regarding EPS produced by *Pediococcus acidilactici* 05B0111 might vary with carbon sources utilized by *Pediococcus acidilactici* 05B0111, and ability of EPS to stimulate TNF-α secretion of macrophages might be hence affected.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

The invention claimed is:

1. A method of producing an exopolysaccharide comprising cultivating an isolated *Pediococcus acidilactici* in a suitable medium under a condition in which the exopolysaccharide is formed, and purifying the exopolysaccharide thus formed, wherein the isolated *Pediococcus acidilactici* is *Pediococcus acidilactici* 05B0111 deposited as *Pediococcus acidilactici* DSM 22345 and is capable of producing an exopolysaccharide; the suitable medium includes a carbon source selected from the group consisting of lactose, fructose, maltose, glucose, molasses, galactose, xylose, xylitol, inulin, sorbitol, trehalose, sucrose, and mixtures thereof; and the suitable medium has a pH of 3 to 5 before the cultivating step.

2. The method of claim 1, wherein the suitable medium is an edible material.

3. The method of claim 2, wherein the edible material is selected from the group consisting of: a fluid milk product, milk powder, fruit juice, soybean milk, vegetable-fruit juice, health food, animal feed, an agricultural product, a livestock product, and an aquatic product.

4. The method of claim 1, wherein, before the cultivating step, the suitable medium has a pH of 5.

5. The method of claim 1, wherein the cultivating step is conducted at a temperature ranging from 25° C. to 37° C.

* * * * *

SEQUENCE LISTING

```
<160> NUMBER OF SEQ ID NOS: 1

<210> SEQ ID NO 1
<211> LENGTH: 513
<212> TYPE: DNA
<213> ORGANISM: Pediococcus acidilactici
<220> FEATURE:
<221> NAME/KEY: misc_feature
<223> OTHER INFORMATION: strain 05B0111

<400> SEQUENCE: 1
agtttgatcc tggctcagga tgaacgctgg cgacgtgcct aatacatgca agtcgaacga      60
acttccgtta attgattatg acgtgcttgc actgatgaga ttttaacacg aagtgagtgg     120
```

-continued

```
cggacgggtg agtaacacgt gggtaacctg cccagaagca ggggataaca cctggaaaca    180
gatgctaata ccgtataaca gagaaaaccg cctggttttc ttttaaaaga tggctctgct    240
atcacttctg gatggacccg cggcgcatta gctagttggt gaggtaacgg ctcaccaagg    300
cgatgatgcg tagccgacct gagagggtaa tcggccacat tgggactgag acacggccca    360
gactcctacg ggaggcagca gtagggaatc ttccacaatg gacgcaagtc tgatggagca    420
acgccgcgtg agtgaagaag ggtttcggct cgtaaagctc tgttgttaaa gaagaacgtg    480
ggtgagagta actgttcacc cagtgacggt att                                 513
```